United States Patent [19]
Powell et al.

[11] 3,985,736
[45] Oct. 12, 1976

[54] N-(SULFUR-SUBSTITUTED)-2H-1,3-THIAZIN-2-YLIDENE NITROMETHYL KETONES AND NITROACETIC ACID ESTERS

[75] Inventors: James E. Powell, Modesto; Steven A. Roman, Oakdale, both of Calif.

[73] Assignee: Shell Oil Company, Houston, Tex.

[22] Filed: July 2, 1975

[21] Appl. No.: 592,432

[52] U.S. Cl. .......................... 260/243 R; 424/246
[51] Int. Cl.² .................................. C07D 279/04

[58] Field of Search .............................. 260/243 R

[56] References Cited
UNITED STATES PATENTS 3,386,997   6/1968   Okumura et al. .................. 260/243

*Primary Examiner*—John M. Ford

[57] ABSTRACT

Novel compounds, identified in the title, useful as insecticides.

2 Claims, No Drawings

N-(SULFUR-SUBSTITUTED)-2H-1,3-THIAZIN-2-YLIDENE NITROMETHYL KETONES AND NITROACETIC ACID ESTERS

DESCRIPTION OF THE INVENTION

It has been found that useful insecticidal activity is possessed by (2H-1,3-thiazin-2-ylidene)nitromethyl ketones and by esters of (2H-1,3-thiazin-2-ylidene)-nitroacetic acids, which are substituted on the ring nitrogen atom by a thio, sulfinyl or sulfonyl moiety. These compounds are described by the formula:

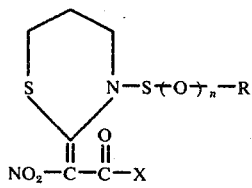

(I)

wherein n is zero, one or two, R is straight-chain or branched-chain alkyl of from one to ten carbon atoms, phenyl or phenyl substituted by one or more of halogen, nitro, cyano, straight-chain or branched-chain alkyl or alkoxy of from 1 to 6 carbon atoms, and X is hydrogen or is $R^1$, $R^1$—O— or $R^1$—S— wherein $R^1$ contains up to thirty carbon atoms and is (a) straight-chain or branched-chain alkyl, alkenyl, alkynyl, haloalkyl, haloalkenyl, mono- and poly(alkoxy)alkyl, alkylthioalkyl, alkylsulfinylalkyl, alkylsulfonylalkyl, cycloalkyl, cycloalkylalkyl, phenylthioalkyl, phenylsulfinylalkyl, phenylsulfonylalkyl; (b) aryl or aralkyl or either substituted on the ring by one to two of one or more of halogen, nitro, cyano, alkyl, aryl, alkoxy or aryloxy; (c) where X is $R^1$—O— or $R^1$—S—, is aminoalkyl, $(CH_2)_mNR^2R^3$, wherein m is one or two, $R^2$ is alkyl, alkenyl, cycloalkyl, aryl or aralkyl and $R^3$ is one of the moieties represented by $R^2$; or (d) is $(CH_2)_n$—$R^4$, wherein n is zero, one or two, and $R^4$ is a heteromonocyclic moiety of from five to six atoms in the ring, containing in the ring carbon atoms and one to two of oxygen (—O—), sulfur (—S—) or nitrogen (—N= or —NH—) bonded to carbon in the ring.

Preferably, the moiety represented by $R^1$ contains no more than ten carbon atoms. The preferred aryl moieties are optionally substituted phenyl. The preferred aminoalkyl moieties are dialkylaminomethyl and -ethyl. The preferred aralkyl moieties are optionally-substituted phenylmethyl. Preferred heterocyclic moieties are furanyl, tetrahydrofuranyl, dioxolanyl, thienyl, thiopyranyl, pyridinyl, pyrrolidinyl, morpholinyl and their -methyl and -ethyl counterparts.

Because of their insecticidal activity characteristics, a preferred sub-class of the genus of the invention consists of these compounds wherein X is lower alkyl, either straight-chain or branched-chain in configuration, and contains, for example, from one to six carbon atoms, R is phenyl and n is 2.

For illustration, preparation of typical species of the genus is described in the examples included hereinafter. Other typical, illustrative species of this genus include those wherein the symbols represent the following moieties, this manner of naming these species being accurate, yet pointing out the differences between the different species more clearly than if the entire, complicated name of each species were to be given:

| R | X | n |
|---|---|---|
| methyl | phenyl | 0 |
| methyl | phenyl | 1 |
| methyl | phenyl | 2 |
| Phenyl | n-propyl | 1 |
| Phenyl | methoxy | 1 |
| methyl | phenoxy | 0 |
| methyl | phenoxy | 1 |
| methyl | phenoxy | 2 |
| methyl | vinyl | 0 |
| methyl | vinyl | 1 |
| methyl | vinyl | 2 |
| methyl | cyclopropylmethoxy | 0 |
| methyl | cyclopropylmethoxy | 1 |
| methyl | cyclopropylmethoxy | 2 |
| Phenyl | methylthio | 0 |
| Phenyl | methylthio | 1 |
| Phenyl | methylthio | 2 |
| methyl | methylthio | 0 |
| methyl | methylthio | 1 |
| methyl | methylthio | 2 |
| 2,4-dinitrophenyl | n-propyl | 0 |
| 4-bromophenyl | n-propyl | 2 |
| 4-chlorophenyl | ethyl | 2 |
| 3-chloropropyl | methoxy | 2 |
| 2,5-dichlorophenyl | methoxy | 2 |
| hexadecyl | ethyl | 2 |
| methyl | methoxy | 2 |
| 4-methoxyphenyl | methoxy | 2 |
| 2-nitrophenyl | phenyl | 2 |
| 4-methylphenyl | phenoxy | 2 |
| trifluoromethyl | propyl | 2 |
| 2-nitrophenyl | ethoxy | 0 |

The compounds of this invention are resonance hybrids, and all may exist as geometric isomers. In this specification, for the sake of simplicity, these compounds are defined in terms of Formula (I). The definition is intended to include all of the contributors to the resonance hybrid and the geometric isomers, as well as mixtures thereof.

Compounds of this invention can be prepared by treatment of an alkali metal (e.g., sodium) derivative of an appropriate thiazine precursor with the appropriate R-sulfenyl chloride, -sulfinyl chloride or -sulfonyl chloride.

The appropriate thiazine precursors are the ketones and esters represented by Formula (I) wherein the ring nitrogen is not substituted.

The ketones are the subject of application Ser. No. 547,417, issued on June 8, 1976, as U.S. Pat. No. 3,962,225, while the esters are the subject of application Ser. No. 554,371 issued on June 8, 1976, as U.S. Pat. No. 3,962,234. For the purpose of describing preparation of said precursors, the pertinent portions of said applications are incorporated herein.

The sulfur-containing reactants — i.e., the sulfenyl-, sulfinyl- and sulfonyl chloride — are in many cases known compounds, and in those cases when they are specifically novel, can be prepared by procedures known in the art for preparing the known analogs thereof.

The thiazine precursors are converted to the needed alkali metal derivatives by treatment with an alkali metal hydride, such as sodium hydride, preferably in a suitable liquid reaction medium, such as tetrahydrofuran, at a low temperature, for example, about 0°–5° C. To enable efficient control of the often exothermic reaction, it may be found desirable to add slowly a solution or suspension of the thiazine to a stirred, cooled solution or suspension of the base, the mixture being stirred further until hydrogen ceases to evolve. The mixture then may be allowed to warm, for example to room temperature, to ensure completion of the reaction.

Treatment of the alkali metal derivative with the sulfur-containing reactant can be effectively carried out under similar conditions: adding the sulfur-containing reactant as a suspension or solution, if necessary, slowly to a stirred solution or suspension of the alkali metal derivative, the reaction mixture being cooled as necessary to maintain it at a low temperature — again, suitably about 0°–5° C — then allowing the stirred mixture to warm, for example to room temperature, and stirring the warmed mixture for a period of time to ensure complete reaction.

It often will be found convenient to employ the same liquid reaction medium in both steps of the process, with tetrahydrofuran or dimethylformamide generally being quite suitable for this purpose. In such a case, the solution or suspension of the alkali metal derivative obtained as the product of the alkali metal hydride-thiazine reaction is treated directly with the solution or suspension of the sulfur-containing reactant.

The desired product can be isolated from the crude reaction mixture and purified by conventional methods, such as filtration, extraction, crystallization and elution (chromatography).

These procedures for preparing compounds of this invention are illustrated in the following examples of the preparation of particular species of such compounds. In all cases the identity of the thiazine precursor was established and the identity of the final product was confirmed by elemental analysis and by infrared and nuclear magnetic resonance spectrum analyses:

EXAMPLE 1 —
1-nitro-1-(tetrahydro-3-(phenylthio)-2H-1,3-thiazin-2-ylidene)-2-pentanone (1)

To a suspension of sodium hydride (from 2.33 g of a 57 % oil dispersion washed free of oil with pentane) in 25 ml of tetrahydrofuran at 0° was added dropwise 11.5 g of 1-nitro-1-(tetrahydro-2H-1,3-thiazin-2-ylidene)-2-pentanone, prepared as described in Example 5 of Ser. No. 547,417, in 100 ml of tetrahydrofuran. The mixture was stirred at about 0° for about 1 hour, then at room temperature over a weekend. The mixture then was cooled to about 0°, a solution of 8.4 g of benzenesulfenyl chloride in 50 ml of tetrahydrofuran was added dropwise, and the mixture was stirred for 3 hours. The mixture was taken up in water and extracted thrice with methylene chloride. The combined extracts were washed with saturated sodium chloride solution and dried ($Na_2SO_4$), and the solvent was evaporated under reduced pressure to give an amber oil. The oil was triturated with ether and filtered, and the filtrate was evaporated under reduced pressure to leave an oil. The oil was chromatographed on silica gel, using a dry column and a solvent system, a 2/8/40 mixture of tetrahydrofuran, ethyl acetate and hexane for development. The bright yellow band was extracted and washed several times with acetone. The solvent was evaporated under reduced pressure to give 1, as an amber oil, boiling point not determined.

EXAMPLE 2 —
1-nitro-1-(tetrahydro-3-(phenylsulfonyl)-2H-1,3-thiazin-2-ylidene)-2-pentanone (2)

The procedure described in Example 1 was repeated, substituting 10.3 g of benzenesulfonyl chloride for the benzenesulfenyl chloride. The crude reaction mixture was diluted with water and extracted thrice with methylene chloride. The combined extracts were washed with saturated sodium chloride solution, and dried ($Na_2SO_4$), and the solvent was evaporated under reduced pressure. The resulting amber oil, dissolved in chloroform, was washed with 5 % sodium hydroxide, water and saturated sodium chloride, dried ($Na_2SO_4$), then passed through Florosil using a 97/3 chloroform/acetone mixture as eluent to give 2, as a yellow solid, m.p.: 87°–89°.

EXAMPLE 3 — Methyl nitro(tetrahydro-3-(phenylthio)-2H-1,3-thiazine-2-ylidene)acetate (3)

1.5 g of sodium hydride in mineral oil was washed free of the oil with pentane. The hydride was stirred in 100 ml of dimethylformamide at 5° and 6.6 g of methyl nitro(tetrahydro-2H-1,3-thiazin-2-ylidene)acetate, prepared as described in Example 2 of Ser. No. 554,371, was added in portions at 5° over a 15-minute period. The mixture was allowed to warm to room temperature, stirred for 30 minutes, and then cooled to 10°. A solution of 5.0 g of benzenesulfenyl chloride in 10 ml of dimethylformamide was added dropwise over a 5-minute period. The mixture was warmed to room temperature and stirred for about 20 hours. Then a few drops of water was added to decompose any remaining sodium hydride and the mixture was poured into methylene chloride. The organic phase was washed with water, dried ($MgSO_4$), decolorized, filtered through Celite, and the solvent was evaporated under reduced pressure to give an orange oil. The oil was triturated with pentane and the solid product was dissolved in ether. The ether solution was washed, dried ($MgSO_4$) and filtered, and the solvent was evaporated under reduced pressure to give a yellow oil. Crystallization from isopropyl alcohol gave 3 as a yellow solid, m.p.: 102.5°–103°.

EXAMPLE 4 — Methyl nitro(tetrahydro-3-(4-methylphenylsulfonyl)-2H-1,3-thiazine-2-ylidene)acetate (4)

The procedure described in Example 3 was repeated, substituting 6.3 g of 4-methylbenzenesulfonyl chloride for the benzenesulfenyl chloride. 4 was obtained by recrystallization from ethanol, as a yellow solid, m.p.: 176°–177° (with decomposition).

EXAMPLE 5 — Methyl nitro(tetrahydro-3-(phenylsulfonyl)-2H-1,3-thiazine-2-ylidene)acetate (4)

The procedure, including work-up procedure, described in Example 4 was repeated substituting 5.8 g of benzenesulfonyl chloride for the 4-methylbenzensulfonyl chloride. 4 was obtained as a solid, m.p.: 123°–4°.

Compounds of this invention exhibit useful insecticidal activity, being of particular interest for control of the larval "caterpillar" or "worm" forms of insects of the genus Heliothis, such as *H. Zea* (corn earworm, cotton bollworm, tomato fruitworm), *H. virescens* (tobacco budworm); the genus Agrotis, such as *A. ipsilon* (black cutworm); the genus Trichoplusia, such as *T. ni* (cabbage looper), and the genus Spodoptera, such as *S. littoralis* (Egyptian cotton leafworm). Some are also of interest for controlling aphids and houseflies. In tests that have been conducted they have exhibited low, or no, toxicity to other insects such as the 2-spotted spider mite and mosquito larvae.

Activity of compounds of this invention with respect to insects was determined by using standardized tests to establish the $LC_{50}$ dosage (in milligrams of test compound per 100 milliliters of solvent or liquid carrier required in the solution or suspension of test compound used) that was required to kill 50 % of the test insects. The test insects were the housefly, corn earworm, pea aphid and 2-spotted spider mite. Activity with respect to mosquito larvae was determined by placing the larvae in water containing the test compound.

All of compounds 1 through 5 were found to be inactive or but slightly active with respect to the mites and mosquito larvae. All were found to be active with respect to the corn earworm. With respect to the houseflies, compounds 1–3 were active while compound 1 was active with respect to the pea aphids.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil or other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers, solid polychlorophenols; bitumen, waxes such as beeswax, paraffin wax and chlorinated mineral waxes; degradable organic solids such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75 % w of toxicant and usually contain, in addition to solid carrier, 3–10 % w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10 % w of toxicant. Granules may be manufactured by agglomeration or impregnation techniques. Generally, granules will contain ½–25 % w toxicant and 0–10 % w of additives such as stabilizers, slow release modifiers and binding agents. Emulsifiable concentrates usually contain, in addition to the solvent, and when necessary, co-solvent, 10–50 % w/v toxicant, 2–20 % w/v emulsifiers and 0–20 % w/v of appropriate additives such as stabilizers, penetrants and corrosion inhibitors. Suspension concentrates are compounded so as to obtain a stable, non-sedimenting, flowable product and usually contain 10–75 % w toxicant, 0–5 % w of dispersing agents, 0.1–10 % w of suspending agents such as protective colloids and thixotropic agents, 0–10 % w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e., the dosage to which the insect contacts — is of the order of 0.001 % to 0.5 % based on the total weight of the formulation, though under some circumstances the effective concentration will be as little as 0.0001 % or as much as 2 %, on the same basis.

I claim as my invention:

1. A compound of the formula:

$$\underset{X-\underset{\|}{C}-\underset{\|}{C}-NO_2}{\underset{O}{\bigvee}}\underset{}{\overset{}{\bigcap}}N-S-(O-R)_n$$

wherein $n$ is zero, one or two, R is straight-chain or branched-chain alkyl of from one to ten carbon atoms, phenyl or phenyl substituted by one or more of halogen, nitro, cyano, straight-chain or branched-chain alkyl or alkoxy of from 1 to 6 carbon atoms, and X is hydrogen or is $R^1$, $R^1$—O— or $R^1$—S— wherein $R^1$ contains up to ten carbon atoms and is a. straight-chain or branched-chain alkyl, alkenyl, alkynyl, haloalkyl, haloalkenyl, mono- and poly(alkoxy)alkyl, alkylthioalkyl, alkylsulfinylalkyl, alkylsulfonylalkyl, cycloalkyl, cycloalkylalkyl, phenylthioalkyl, phenylsulfinylalkyl, phenylsulfonylalkyl;

b. phenyl or phenalkyl or either substituted on the ring by one to two of one or more of halogen, nitro, cyano, alkyl, phenyl, alkoxy or phenoxy;

c. where X is $R^1$—O— or $R^1$—S—, $R^1$ is $-(CH_2)_m NR^2 R^3$, wherein $m$ is one or two, $R^2$ is alkyl, alkenyl, cycloalkyl, phenyl or phenalkyl and $R^3$ is one of the moieties represented by $R^2$; or d. is $-(CH_2)_n-R^4$, wherein $n$ is zero, one or two, and $R^4$ is one of furanyl, tetrahydrofuranyl, dioxolanyl, thienyl, thiopyranyl, pyridinyl, pyrrolidinyl, morpholinyl and their -methyl and -ethyl counterparts.

2. A compound according to claim 1 wherein X is lower alkyl, R is phenyl and $n$ is 2.

* * * * *